United States Patent
Zuckerman

(10) Patent No.: US 6,998,112 B2
(45) Date of Patent: Feb. 14, 2006

(54) SLEEP INDUCING TOOTHPASTE MADE WITH NATURAL HERBS AND A NATURAL HORMONE

(76) Inventor: Arthur Zuckerman, 614 Second Ave., Suite D, New York, NY (US) 10016

(*) Notice: Subject to any disclaimer, the term of this patent is extended or adjusted under 35 U.S.C. 154(b) by 46 days.

(21) Appl. No.: 10/391,004

(22) Filed: Mar. 18, 2003

(65) Prior Publication Data

US 2004/0185014 A1    Sep. 23, 2004

(51) Int. Cl.
*A61K 7/16*    (2006.01)
*A61K 7/26*    (2006.01)

(52) U.S. Cl. .......................... 424/58; 424/49; 424/725; 424/729; 424/733; 424/736; 424/764; 514/923

(58) Field of Classification Search .................. 424/49, 424/58, 725, 729, 733, 736, 764
See application file for complete search history.

(56) References Cited

U.S. PATENT DOCUMENTS 5,043,153 A * 8/1991 Videki et al. .................. 424/49
5,591,768 A * 1/1997 Lewy et al. .................. 514/415
6,200,550 B1 * 3/2001 Masterson et al. ............. 424/49
6,469,044 B1 * 10/2002 Zisapel ........................ 514/415
6,509,007 B1 * 1/2003 Rajaiah et al. ................ 424/53

OTHER PUBLICATIONS

Chemical Abstracts 137:24166, "Oral hygeine composition for promoting the onset of sleep", abstract of Italian language patent 1299082, published Apr. 15, 1998.*
English languge translation of Italian Patent No. 01299082 (Apr. 15, 1998).*

* cited by examiner

*Primary Examiner*—Frederick Krass
(74) *Attorney, Agent, or Firm*—Ezra Sutton, Esq.

(57) ABSTRACT

A toothpaste composition for inducing sleep while simultaneously promoting intraoral cleanliness, which includes toothpaste base ingredients and at least one sleep-inducing natural herb or hormone. The sleep-inducing natural herbs and hormone are selected from the group consisting of Chamomile, Lemon Balm, Passion Flower, and Valerian, and the hormone Melatonin. The sleep-inducing natural herbs are in a range of 0.25% to 18% by weight of the composition.

4 Claims, No Drawings

SLEEP INDUCING TOOTHPASTE MADE WITH NATURAL HERBS AND A NATURAL HORMONE

FIELD OF THE INVENTION

The following natural herbs and natural hormone in combination with toothpaste is used at night to improve sleep. The expected dose of toothpaste is calculated at 2 grams. The ingredients have been assessed for range of daily dose for best effects, toxicity in normal range, recommended proportion of each, and water solubility of key constituents.

BACKGROUND OF THE INVENTION

It is an object of the present invention to provide a sleep-inducing toothpaste or mouth spray which includes sleep-inducing natural herbs and a natural hormone.

It is a further object of the present invention to provide a sleep-inducing toothpaste which includes toothpaste base ingredients and natural herbs being Chamomile, Lemon Balm, Passion Flower, Valerian and the natural hormone Melatonin.

SUMMARY OF THE INVENTION

A toothpaste composition is provided for inducing sleep while simultaneously promoting intraoral cleanliness, which includes toothpaste base ingredients and at least one sleep-inducing natural herb or hormone. The sleep-inducing natural herbs and hormone are selected from the group consisting of the natural herbs Chamomile, Lemon Balm, Passion Flower, and Valerian, and the natural hormone Melatonin. The sleep-inducing natural herbs are in a range of 0.25% to 18% by weight of the composition, which may be in the form of a dental cream or mouth spray.

DESCRIPTION OF THE PREFERRED EMBODIMENTS

The toothpaste composition has base ingredients which comprise a combination of known amounts of: Vegetable Glycerin; Sorbitol; Hydrated Silica; Purified Water; Xylitol; Carrageenan; Sodium Lauryl Sulfate; Titanium Dioxide; Propylparaben; Methylparaben; Sodium Benzoate; and a flavoring agent.

The sleep-inducing natural herbs include the following:

A) Name: Chamomile, Camomile

Scientific Name: *Matricaria recutita, Matricaria chamomilla* (German), *Anthemis nobilis* (Roman)

Chamomile comprises substantially ½ to 3% by weight of the toothpaste composition and preferably comprises substantially 1% by weight of the composition.

Chamomile, a member of the daisy family, is native to Europe and western Asia. German chamomile is the most commonly used. German Chamomile is a Southern European annual plant found wild along roadsides, in fields, and cultivated in gardens. It is chiefly grown for commerce in Egypt.

Roman chamomile is a low European perennial found in dry fields and around gardens and cultivated grounds, cultivated in Eastern Europe.

Parts Used: Flowers. Roman flowers are hollow while *Matricaria* flowers are solid.

In the proposed toothpaste chamomile has potential for the treatment of:

Canker sores (mouth ulcers)
Gingivitis (periodontal disease)

Daily Dose Range for Prime Efficacy:

2–4 grams of the ground, dried herb in capsules or tablets, 1–3 times a day.

1:5 tincture: 5–15 ml, 1–3 times per day, best between or before meals or at bedtime.

1:2 tincture: 3–6 ml, prn, h.s.

1% of a 1:2 extract. Its presence is important but the desired effect (sleep) will depend on substantial concentrations of two other strong sedatives, Valerian and Passionflower, synergistically supported by adequate amounts of the rest.

Safety and Toxicity in Recommended Dosage Range:

Though extremely rare, allergic reactions to chamomile have been reported. These reactions have included bronchial constriction with internal use and allergic skin reactions with topical use.

FDA lists chamomile as generally regarded as safe. There is no restriction on long term use. It is given in material doses and as a homeopathic preparation to teething babies.

Active Compounds:

The flowers of chamomile provide 0.5–1.5% volatile oils containing (–) alpha-bisabolol, alpha-bisabolol oxides A & B, and matricine (usually converted to chamazulene by water and heat, i.e. steam distillation or make a tea).

Other active constituents include the bioflavonoids apigenin, luteolin, and quercitin (0.5–3%). Apigenin is one of several constituents hypothesized to create mild sedative effects observed in animal experiments (Mills and Bone p322).

The European Pharmacopoeia recommends 4 ml/kg or more of blue essential oil. These active ingredients contribute to chamomile's anti-inflammatory, antispasmodic, and smooth muscle-relaxing effects, particularly in the gastrointestinal tract.

History:

Chamomile has been used for centuries as a medicinal plant, mostly for gastrointestinal complaints though it has therapeutic value in a wide variety of conditions. It is used in various parts of the world as a beverage tea. Chamomile is used in many nervous diseases, and is a gentle hypnotic (aids in falling asleep). As a mild sedative and emmenagogue it is used to regulate painful periods.

B) Name: Lemon Balm

Scientific Name: *Melissa officinalis*

Family: Lamiacease, the Mint Family

Parts used: Herb, leaves, volatile oil and polyphenols.

Lemon Balm comprises substantially ½ to 3% by weight of the toothpaste composition and preferably comprises substantially 1% by weight of the composition.

In the proposed toothpaste lemon balm has potential for the treatment of:

insomnia
headaches
restlessness
toothache
viral sores
minor digestive spasm

Daily Dose Range for Prime Efficacy:

2–3 grams of the ground, dried herb in capsules or tablets, 1–3 times a day.

1:5 tincture: 2–6 ml, 1–3 times per day, best between or before means or one daily dose at bedtime.

1:2 tincture: 1–3 ml, as needed, or one daily dose at bedtime.

Tea: 1 ounce of leaves, stems, flowers to a pint of water. Boil water, pour over herb, steep 5 to 10 minutes, drink 1–2 cups or more per day.

Recommended Percent in Toothpaste Formula: 1% due to Lemon Balm's potent flavor and its mild sedative properties. When bruised, the aerial parts smell like lemon and mint. Fresh plant material may be used if it meets pharmacopoeia standards when a sample is dried.

Safety and Toxicity in Recommended Dosage Range:

No restrictions for ingestion or topical use are found.

US: Generally recognized as safe

UK: General sales list

Canada: approved as an over-the-counter drug

France: Traditional Medicine

Germany: Commission E approved as an over the counter drug.

Active Compounds:

Essential oil 0.06–0.375% with monoterpene aldehydes geranial & neral (Citral a & b), citronellal Flavonoids apigenin, luteolin, kaempferol, quercetin Glycosides Up to 4% rosmarinic acid, anti-inflammatory and antioxidant Ursolic, oleanolic acids Sedative effects long appreciated in folk medicine have been confirmed only in animal experiments using water/alcohol extracts given by injection.

C) Name: Passion Flower

Scientific Name: *Passiflora incarnata*

Family: Passifloraceae

Parts Used: The leaves, stems, and flower before the vine fruits.

In the proposed toothpaste Passionflower has potential for the treatment of:

Insomnia

Muscle spasm

Pain

Emotional upset

Viral sores

Passion Flower comprises substantially 1 to 4% by weight of the toothpaste composition and preferably comprises substantially 2% by weight of the composition.

Passion flower has a depressant effect on the Central Nervous System. The herb is used for its sedative properties, to lower blood pressure, and prevent tachycarduia. The alkaloid and flavonoids have both been reported to have sedative activity in animals.

Many of the flavonoids, such as apigenin, are well-known for pharmacological activity, particularly anti-spasmodic and anti-inflammatory activities. It is the herb of choice for treating intransigent insomnia.

Daily Dose Range for Prime Efficacy:

2–4 grams of the ground, dried herb in capsules or tablets, 1–3 times a day.

1:5 tincture: 6–12 ml, 1–3 times per day, or one daily dose all at bedtime.

1:2 tincture: 2–4 ml, as needed, or one daily dose all at bedtime.

Recommended Percent in Toothpaste Formula: 2%

Safety and Toxicity in Recommended Dosage Range:

Passion flower is generally safe and has not been found to negatively interact with other sedative drugs. The American Botanical Safety Handbook lists Passion Flower as category 1-no restrictions.

Active Compounds:

Alkaloids: harmine, harman, harmol, harmaline, harmalol, and passaflorine.

No less than 8% flavonoids: apigenin and various glycosides, homo-orientin, isovitexin, kaempferol, luteolin, orientin, quercitin, rutin, saponaretin, saponarin and vitexin. The flavonoids in passion flower are the primary constituents responsible for its relaxing and anti-anxiety effects.

D) Name: Valerian

Scientific Name: *Valeriana officinalis*

Family: Valerianaceae

Parts Used: Root and rhizome.

In the proposed toothpaste Valerian has potential for the treatment of:

Insomnia

Pain

Blood Pressure

Valerian comprises substantially 3 to 6% by weight of the toothpaste composition and preferably comprises substantially 4% by weight of the composition.

Daily Dose Range for Prime Efficacy:

A wide range experimentally and in clinical trials exists, from a minimum of 60–120 mg per dose up to 300–500 mg of the ground, dried herb in capsules or tablets, 1–3 times a day or one daily dose 1 hour before bedtime.

Recommended Percent in Toothpaste Formula: 4% This amount reflects this herb's primacy in an oral, water-extracted, herbal formula designed for helping sleep.

Safety and Toxicity in Recommended Dosage Range:

No adverse effects are expected when taken within recommended dosage ranges. The FDA lists valerian as generally safe.

Valerian has a long history of exceptional safety, which has been confirmed by clinical studies.

Active Compounds:

0.35–1% essential oils (not less than 5 ml/kg) including monoterpenes (borneol), sesquiterpenes (beta-bisabolene, valerenal in fresh root), esters of valerianic, isovalerianic acid Iridoids, 0.5%–2%, a.k.a. valepotriates and decomposition products including valtrate, isovlatrate, dihidrovaltrate, acevaltrate Valerenic acid, its derivatives Aminos, lignans The essential oil (aroma and flavor) contribute perhaps ⅓ to the sedating properties of the herb. Many constituents are thought to synergize for its sedative effects. Central nervous system sedation is regulated by receptors in the brain known as GABA-A receptors. Valerian weakly binds to these receptors for a sedating effect.

Clinical studies have shown that people taking valerian had shown significantly improved sleep quality without morning grogginess. Some researchers have compared valerian to benzodiazepines such as Valium (to which it bears no relation, either etymologically or as a source for drug development). However, valerian is a much milder and safer sedative. Unlike Valium, valerian is not addictive or does not promote dependency. Valerian's sedative effect is not significantly exaggerated by alcohol and barbiturates, unlike Valium. Valerian extract at a dose of 50 to 100 mg taken two or three times daily has been shown to relieve performance anxiety and the stress of driving in heavy traffic. Larger doses of valerian extract may be necessary for patients who have been using benzodiazepine prescriptions for anxiety.

E) Name: Melatonin

The chemical symbol for the natural hormone Melatonin is:

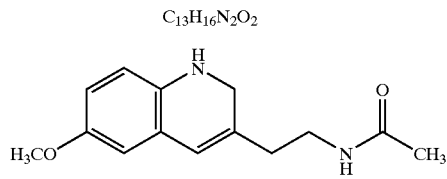

$C_{13}H_{16}N_2O_2$

In the proposed toothpaste has potential for the treatment of:

Sleep disorders

Daily Dose Range for Prime Efficacy:

1 to 20 mg; thirty minutes before retiring. For sleeplessness due to low melatonin, the dosage range is 2–10 mg. The lower dose may be taken for at least three days, then gradually increased by 1–2 mg every three nights up to 15 mg if results are not what expected. Higher doses, 20 mg up to 50 mg, have been used for patients on chemotherapy.

Recommended Percent in Toothpaste Formula:

Melatonin comprises substantially 0.25% to 2% by weight of the toothpaste composition and preferably comprises substantially 0.50% by weight of the composition.

Percent depends on milligrams one dose of toothpaste can provide. The more there is the better the change that some will be absorbed orally. In a 2 gram dose of toothpaste 10 mg of melatonin may be the upper limit that can be accommodated. Though this may be effective as much as possible, up to 20 mg, is recommended since toothpaste isn't swallowed.

Safety and Toxicity in Recommended Dosage Range:

No toxicity is expected though studies of melatonin's safety are limited, with isolated reports of exacerbation of depression and fatigue.

History:

Melatonin has been called the body's own natural sleeping pill. It plays a key role in the sleep cycle by helping one fall asleep. Low melatonin levels can cause sleep-onset insomnia. The body changes serotonin into melatonin, a hormone stored in the pineal gland. The pineal releases melatonin only when the level of light is low. For most people melatonin is secreted only at night, during sleep unless lights are left on. The presence of light is a sign to the brain to shut down melatonin production.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A toothpaste for inducing sleep while simultaneously promoting intraoral cleanliness, comprising:
   a) a combination of sleep-inducing herbs comprising:
      i) ½ to 3 percent by weight chamomile;
      ii) ½ to 3 percent by weight lemon balm;
      iii) 1 to 4 percent by weight passion flower;
      iv) 3 to 6 percent by weight valerian; and
   b) 0.25 to 2 percent by weight melatonin;
   wherein all percentages are based on the weight of the toothpaste composition.

2. A toothpaste for inducing sleep while simultaneously promoting intraoral cleanliness, comprising:
   a) a combination of sleep-inducing herbs comprising:
      i) 1 percent by weight chamomile;
      ii) 1 percent by weight lemon balm;
      iii) 2 percent by weight passion flower;
      iv) 4 percent by weight valerian; and
   b) 0.50 percent by weight melatonin;
   wherein all percentages are based on the weight of the toothpaste composition.

3. A toothpaste for inducing sleep while simultaneously promoting intraoral cleanliness, comprising:
   a) a combination of sleep-inducing herbs comprising:
      i) ½ to 3 percent by weight lemon balm;
      ii) 1 to 4 percent by weight passion flower;
      iiii) 3 to 6 percent by weight valerian; and
   b) 0.25 to 2 percent by weight melatonin;
   wherein all percentages are based on the weight of the toothpaste composition.

4. A toothpaste for inducing sleep while simultaneously promoting intraoral cleanliness, comprising:
   a) a combination of sleep-inducing herbs comprising:
      i) 1 percent by weight lemon balm;
      ii) 2 percent by weight passion flower;
      iii) 4 percent by weight valerian; and
   b) 0.50 percent by weight melatonin;
   wherein all percentages are based on the weight of the toothpaste composition.

* * * * *